US012558116B2

(12) United States Patent (10) Patent No.: US 12,558,116 B2
Pigott et al. (45) Date of Patent: Feb. 24, 2026

(54) INTRAVASCULAR DEVICE FOR TREATING FISTULAS

(71) Applicant: VentureMed Group, Inc., Plymouth, MN (US)

(72) Inventors: John P. Pigott, Sylvania, OH (US); Jenny Zeroni, Plymouth, MN (US); Adam Tschida, Brooklyn Park, MN (US)

(73) Assignee: VentureMed Group, Inc., Plymouth, MN (US)

( * ) Notice: Subject to any disclaimer, the term of this patent is extended or adjusted under 35 U.S.C. 154(b) by 1005 days.

(21) Appl. No.: 17/702,344

(22) Filed: Mar. 23, 2022

(65) Prior Publication Data

US 2023/0301679 A1 Sep. 28, 2023

(51) Int. Cl.
 *A61B 17/3209* (2006.01)
 *A61B 17/3207* (2006.01)
 *A61B 17/00* (2006.01)
 *A61M 25/00* (2006.01)
(52) U.S. Cl.
 CPC .. *A61B 17/320725* (2013.01); *A61B 17/3209* (2013.01); *A61B 2017/00292* (2013.01); *A61B 2017/00986* (2013.01); *A61B 2217/005* (2013.01); *A61B 2217/007* (2013.01); *A61M 25/0082* (2013.01)
(58) Field of Classification Search
 CPC .. A61M 2025/1084; A61M 2025/1086; A61M 2025/109; A61B 17/3207; A61B 17/320725; A61B 17/3209; A61B 2017/00986
 See application file for complete search history.

(56) References Cited

U.S. PATENT DOCUMENTS

| | | | |
|---|---|---|---|
| 2,655,154 A | 10/1953 | Richter |
| 3,557,794 A | 1/1971 | Van Patten |
| 3,704,711 A | 12/1972 | Park |
| 4,273,128 A | 6/1981 | Banning |
| | (Continued) | |

FOREIGN PATENT DOCUMENTS

| | | |
|---|---|---|
| EP | 0727194 A1 | 8/1996 |
| WO | 8102109 A1 | 8/1981 |
| | (Continued) | |

OTHER PUBLICATIONS

Cardiovascular Systems Inc., Diamondback 360 Coronary Orbital Atherectomy System, http://www.csi360.com/products/coronary-diamondback-360-coronary-orbital-atherectomy-system-crowns/, 2016.

(Continued)

*Primary Examiner* — Laura A Bouchelle
(74) *Attorney, Agent, or Firm* — Standley Law Group LLP; Adam J. Smith; Jeffrey S. Standley

(57) ABSTRACT

An intravascular device for treating a fistula and methods of using the same are provided. A catheter tube extends from a handle assembly and is attached to an expandable portion which is selectively movable between a first position and an expanded position. Incising elements located at the expandable portion have tapered profiles for creating incisions in tissue accumulated at the fistula upon axial retraction through the fistula. Irrigation or suction devices may be provided.

21 Claims, 8 Drawing Sheets

(56)  References Cited

U.S. PATENT DOCUMENTS

| | | | |
|---|---|---|---|
| 4,292,974 A | 10/1981 | Fogarty et al. | |
| 4,654,027 A | 3/1987 | Dragan et al. | |
| 5,030,201 A * | 7/1991 | Palestrant | A61B 17/320725 |
| | | | 600/568 |
| 5,074,817 A | 12/1991 | Song | |
| 5,074,871 A | 12/1991 | Groshong | |
| 5,100,425 A | 3/1992 | Fischell et al. | |
| 5,154,724 A | 10/1992 | Andrews | |
| 5,156,610 A | 10/1992 | Reger | |
| 5,178,625 A | 1/1993 | Groshong | |
| 5,190,525 A | 3/1993 | Oswald et al. | |
| 5,211,651 A | 5/1993 | Reger et al. | |
| 5,224,945 A | 7/1993 | Pannek, Jr. | |
| 5,244,619 A | 9/1993 | Burnham | |
| 5,246,421 A | 9/1993 | Saab | |
| 5,250,060 A | 10/1993 | Carbo et al. | |
| 5,282,484 A | 2/1994 | Reger | |
| 5,312,427 A | 5/1994 | Shturman | |
| 5,318,576 A | 6/1994 | Plassche, Jr. et al. | |
| 5,376,100 A | 12/1994 | Lefebvre | |
| 5,514,093 A | 5/1996 | Ellis et al. | |
| 5,591,194 A | 1/1997 | Berthiaume | |
| 5,658,309 A | 8/1997 | Berthiaume et al. | |
| 5,665,098 A | 9/1997 | Kelly et al. | |
| 5,676,654 A | 10/1997 | Ellis et al. | |
| 5,697,944 A * | 12/1997 | Lary | A61B 17/3209 |
| | | | 606/159 |
| 5,697,948 A | 12/1997 | Marin et al. | |
| 5,728,067 A | 3/1998 | Enger | |
| 5,728,123 A | 3/1998 | Lemelson et al. | |
| 5,733,296 A | 3/1998 | Rogers et al. | |
| 5,766,192 A | 6/1998 | Zacca | |
| 5,792,158 A | 8/1998 | Lary | |
| 5,800,450 A | 9/1998 | Lary et al. | |
| 5,836,868 A | 11/1998 | Ressemann et al. | |
| 5,876,448 A | 3/1999 | Thompson et al. | |
| 5,961,536 A | 10/1999 | Mickley et al. | |
| 5,968,064 A | 10/1999 | Selmon et al. | |
| 6,071,287 A | 6/2000 | Verbeek | |
| 6,120,515 A | 9/2000 | Rogers et al. | |
| 6,129,708 A | 10/2000 | Enger | |
| 6,165,187 A | 12/2000 | Reger | |
| 6,217,549 B1 | 4/2001 | Selmon et al. | |
| 6,258,108 B1 | 7/2001 | Lary | |
| 6,270,489 B1 | 8/2001 | Wise et al. | |
| 6,283,947 B1 | 9/2001 | Mirzaee | |
| 6,527,740 B1 | 3/2003 | Jackson et al. | |
| 6,599,267 B1 | 7/2003 | Ray et al. | |
| 6,692,466 B1 | 2/2004 | Chow et al. | |
| 6,695,863 B1 | 2/2004 | Ramzipoor et al. | |
| 6,719,773 B1 | 4/2004 | Boucher et al. | |
| 6,884,257 B1 | 4/2005 | Cox | |
| 7,108,704 B2 | 9/2006 | Trerotola | |
| 7,131,981 B2 | 11/2006 | Appling et al. | |
| 7,172,614 B2 | 2/2007 | Boyle et al. | |
| 7,279,002 B2 | 10/2007 | Shaw et al. | |
| 7,303,572 B2 | 12/2007 | Melsheimer et al. | |
| 7,329,267 B2 | 2/2008 | Weber | |
| 7,517,352 B2 | 4/2009 | Evans et al. | |
| 7,686,824 B2 | 3/2010 | Konstantino et al. | |
| 7,691,086 B2 | 4/2010 | Tkebuchava | |
| 7,708,753 B2 | 5/2010 | Hardert | |
| 7,850,685 B2 | 12/2010 | Kunis et al. | |
| 7,850,710 B2 | 12/2010 | Huss | |
| 7,887,557 B2 | 2/2011 | Kelley et al. | |
| 7,914,549 B2 | 3/2011 | Morsi | |
| 7,955,350 B2 | 6/2011 | Konstantino et al. | |
| 8,308,754 B2 | 11/2012 | Belson | |
| 8,323,307 B2 | 12/2012 | Hardert | |
| 8,328,829 B2 | 12/2012 | Olson | |
| 8,348,987 B2 | 1/2013 | Eaton | |
| 8,366,661 B2 | 2/2013 | Weber et al. | |
| 8,398,662 B2 | 3/2013 | Granada et al. | |
| 8,430,904 B2 | 4/2013 | Belson | |
| 8,454,636 B2 | 6/2013 | Konstantino et al. | |
| 8,500,789 B2 | 8/2013 | Wuebbeling et al. | |
| 8,685,049 B2 | 4/2014 | Schur et al. | |
| 8,685,050 B2 | 4/2014 | Schur et al. | |
| 8,702,736 B2 | 4/2014 | Schur et al. | |
| 8,740,849 B1 | 6/2014 | Fischell et al. | |
| 8,870,816 B2 | 10/2014 | Chambers et al. | |
| 8,968,354 B2 | 3/2015 | Wang et al. | |
| 8,974,490 B2 | 3/2015 | Jonsson | |
| 9,039,727 B2 | 5/2015 | Kusleika | |
| 9,079,000 B2 | 7/2015 | Hanson et al. | |
| 9,192,747 B2 | 11/2015 | Hardert | |
| 9,282,991 B2 | 3/2016 | Schur et al. | |
| 9,314,329 B2 | 4/2016 | Dickinson et al. | |
| 9,364,255 B2 | 6/2016 | Weber | |
| 9,364,284 B2 | 6/2016 | Groff et al. | |
| 9,510,901 B2 | 12/2016 | Steinke et al. | |
| 9,532,798 B2 | 1/2017 | Schur et al. | |
| 9,545,263 B2 | 1/2017 | Lenihan et al. | |
| 9,592,386 B2 | 3/2017 | Mathur et al. | |
| 9,604,036 B2 | 3/2017 | Burton et al. | |
| 9,615,848 B2 | 4/2017 | Pigott | |
| 10,463,387 B2 | 11/2019 | Pigott | |
| 10,485,572 B2 | 11/2019 | Pigott | |
| 10,610,255 B2 * | 4/2020 | Pigott | A61M 25/0074 |
| 10,820,921 B2 * | 11/2020 | Randall | A61B 17/320725 |
| 10,842,971 B2 | 11/2020 | Iwano et al. | |
| 10,874,837 B2 | 12/2020 | Iwano et al. | |
| 2001/0007059 A1 | 7/2001 | Mirzaee | |
| 2002/0010489 A1 | 1/2002 | Grayzel et al. | |
| 2002/0029052 A1 | 3/2002 | Evans et al. | |
| 2002/0143350 A1 | 10/2002 | Heitzmann et al. | |
| 2002/0143362 A1 | 10/2002 | Macovial et al. | |
| 2002/0161394 A1 | 10/2002 | Macoviak et al. | |
| 2003/0069547 A1 | 4/2003 | Gonon | |
| 2003/0125756 A1 | 7/2003 | Shturman et al. | |
| 2003/0144677 A1 | 7/2003 | Lary | |
| 2003/0208215 A1 | 11/2003 | Uflacker | |
| 2004/0034384 A1 | 2/2004 | Fukaya | |
| 2004/0098014 A1 | 5/2004 | Flugelman | |
| 2004/0122457 A1 | 6/2004 | Weber | |
| 2004/0204738 A1 | 10/2004 | Weber et al. | |
| 2004/0267345 A1 | 12/2004 | Lorenzo et al. | |
| 2005/0055077 A1 | 3/2005 | Marco et al. | |
| 2005/0149102 A1 | 7/2005 | Radisch, Jr. et al. | |
| 2005/0149159 A1 | 7/2005 | Andreas et al. | |
| 2005/0151304 A1 | 7/2005 | Boelens et al. | |
| 2005/0240176 A1 | 10/2005 | Oral et al. | |
| 2006/0020285 A1 | 1/2006 | Niermann | |
| 2006/0089637 A1 | 4/2006 | Werneth et al. | |
| 2006/0111736 A1 | 5/2006 | Kelley | |
| 2006/0116701 A1 | 6/2006 | Crow | |
| 2006/0184191 A1 | 8/2006 | O'Brien | |
| 2006/0253148 A1 | 11/2006 | Leone et al. | |
| 2007/0005093 A1 | 1/2007 | Cox | |
| 2007/0060863 A1 | 3/2007 | Goeken et al. | |
| 2007/0083194 A1 | 4/2007 | Kunis et al. | |
| 2007/0106215 A1 | 5/2007 | Olsen et al. | |
| 2007/0156225 A1 | 7/2007 | George et al. | |
| 2007/0181157 A1 | 8/2007 | Dadourian | |
| 2008/0140051 A1 | 6/2008 | Bei et al. | |
| 2008/0294116 A1 | 11/2008 | Wolter et al. | |
| 2008/0300594 A1 | 12/2008 | Goto | |
| 2008/0300610 A1 | 12/2008 | Chambers | |
| 2009/0099583 A1 | 4/2009 | Butterfield et al. | |
| 2009/0105686 A1 | 4/2009 | Snow et al. | |
| 2009/0192508 A1 | 7/2009 | Laufer et al. | |
| 2009/0204068 A1 | 8/2009 | Nguyen et al. | |
| 2009/0254172 A1 | 10/2009 | Grewe | |
| 2009/0306690 A1 | 12/2009 | Rivers et al. | |
| 2009/0312807 A1 | 12/2009 | Boudreault et al. | |
| 2010/0010521 A1 | 1/2010 | Kurrus | |
| 2010/0023035 A1 | 1/2010 | Kontos | |
| 2010/0076482 A1 | 3/2010 | Shu et al. | |
| 2010/0121270 A1 | 5/2010 | Gunday et al. | |
| 2010/0168737 A1 | 7/2010 | Grunewald | |
| 2010/0168778 A1 | 7/2010 | Braido | |
| 2010/0330147 A1 | 12/2010 | Hossainy et al. | |
| 2011/0060182 A1 | 3/2011 | Kassab et al. | |
| 2011/0152683 A1 | 6/2011 | Gerrans et al. | |

(56) References Cited

U.S. PATENT DOCUMENTS

| | | |
|---|---|---|
| 2011/0160645 A1 | 6/2011 | Sutermeister et al. |
| 2011/0184447 A1 | 7/2011 | Leibowitz et al. |
| 2011/0288479 A1 | 11/2011 | Burton |
| 2012/0053485 A1 | 3/2012 | Bloom |
| 2012/0143054 A1 | 6/2012 | Eaton et al. |
| 2012/0150142 A1 | 6/2012 | Weber et al. |
| 2012/0157988 A1 | 6/2012 | Stone et al. |
| 2012/0172901 A1 | 7/2012 | Manderfeld et al. |
| 2013/0066346 A1 | 3/2013 | Pigott |
| 2013/0116715 A1 | 5/2013 | Weber |
| 2013/0131594 A1 | 5/2013 | Bonnette et al. |
| 2013/0150874 A1 | 6/2013 | Kassab |
| 2013/0237950 A1 | 9/2013 | Gianotti et al. |
| 2013/0253467 A1 | 9/2013 | Gianotti et al. |
| 2014/0121672 A1 | 5/2014 | Folk |
| 2014/0257367 A1 | 9/2014 | Jonsson |
| 2014/0257368 A1 | 9/2014 | Jonsson |
| 2014/0277002 A1 | 9/2014 | Grace |
| 2014/0350523 A1 | 11/2014 | Dehdashtian et al. |
| 2014/0364896 A1 | 12/2014 | Consigny |
| 2014/0371783 A1 | 12/2014 | Shu et al. |
| 2015/0133978 A1 | 5/2015 | Paul, Jr. |
| 2015/0182324 A1 | 7/2015 | Naor et al. |
| 2016/0143721 A1 | 5/2016 | Rosenbluth et al. |
| 2017/0056048 A1 | 3/2017 | Erpen |
| 2017/0079679 A1 | 3/2017 | Pigott |
| 2017/0238960 A1 | 8/2017 | Hatta et al. |
| 2018/0177985 A1 | 6/2018 | Nakagawa et al. |
| 2019/0307992 A1 | 10/2019 | Haverkost et al. |
| 2020/0289102 A1 | 9/2020 | Wilson et al. |
| 2020/0297376 A1 | 9/2020 | Marks et al. |
| 2021/0023347 A1 | 1/2021 | Iwano et al. |
| 2021/0220008 A1 | 7/2021 | Pigott |

FOREIGN PATENT DOCUMENTS

| | | | |
|---|---|---|---|
| WO | 9502370 | A2 | 1/1995 |
| WO | 1996039997 | A2 | 12/1996 |
| WO | 9918862 | A1 | 4/1999 |
| WO | 02078511 | A2 | 10/2002 |
| WO | 02078511 | A3 | 10/2002 |
| WO | 2007095125 | A2 | 8/2007 |
| WO | 2013159066 | A1 | 10/2013 |
| WO | 2013169596 | A1 | 11/2013 |
| WO | 2014106226 | A2 | 7/2014 |
| WO | 2014142801 | A1 | 9/2014 |
| WO | 2015190578 | A1 | 12/2015 |
| WO | 2015195606 | A1 | 12/2015 |
| WO | 2016210167 | A1 | 12/2016 |

OTHER PUBLICATIONS

Boston Scientific Corporation, FilterWire EZ, Embolic Protection System for Carotid Arteries, Sep. 2015, http://www.bostonscientific.com/en-US/products/embolic-protection/filterwire-ez-embolic-protection-system.html.

International Search Report, Application No. PCT/US2012/055079, dated Jan. 31, 2013.

Boston Scientific, Rotablator Rotational Atherectomy System, http://www.bostonscientific.com/en-US/products/plaque-modification/rotablator-rotational-atherectomy-system.html, 2017.

Covidien, SpiderFX Embolic Protection Device, 2015, https://www.ev3.net/peripheral/us/embolic-protection/spiderfxtrade-embolic-protection-device.htm.

Boston Scientific, Sterling 0.018" Balloon Catheter, Jun. 2015.

Ham, S. et al., Safety of Carbon Dioxide Digital Subtraction Angiography, Archives of Surgery, Dec. 2011.

Alexander, J., CO2 Angiography in Lower Extremity Arterial Disease, Endovascular Today, Sep. 2011, pp. 27-34.

* cited by examiner

INTRAVASCULAR DEVICE FOR TREATING FISTULAS

CROSS-REFERENCE TO RELATED APPLICATIONS

This application makes no priority claim.

FIELD OF THE INVENTION

These disclosures relate, in general, to intravascular devices, such as can be used during minimally invasive surgical procedures. In particular, these disclosures relate to an intravascular device having AV fistula/graft treatment elements.

BACKGROUND AND SUMMARY OF THE INVENTION

Fistulas are abnormal connections between organs. Sometimes, an artery and a vein are artificially connected to create an AV fistula or graft, such as using a patient's own blood vessels, artificial implants, cadaver and/or donated blood vessels, combinations thereof, or the like. The terms "fistula" or "AV fistula" may be used herein to generally describe surgically created fistulas which connect blood vessels. AV fistulas are sometimes needed for certain procedures, or to withstand the rigors of certain treatments. For example, without limitation, AV fistulas are sometimes created for dialysis treatment to provide an access point which may be accessed frequently (e.g., several times a week) without collapsing the vessels.

AV fistulas are known to sometimes experience stenosis, which can cause damage or failure of the AV fistula. The mechanism and type of stenosis is generally different from that of other types of blood vessel stenosis (e.g., plaque accumulation). For example, without limitation, the stenosis of AV fistulas may comprise fibrotic tissue, which is sometimes more difficult to incise or otherwise treat than atherosclerotic material. Conventional stenosis devices (e.g., angioplasty, stents, and tissue removal devices) may not be well suited for treating the fibrotic tissue commonly found in AV fistulas.

Intravascular devices having AV fistula treatment elements are disclosed. The intravascular devices may include some or all of the same or similar components as shown and/or described in in U.S. Pat. No. 9,615,848 issued Apr. 11, 2017, US Pub. No. 2021/0220008 published Jul. 22, 2021, the disclosures of which are hereby incorporated by reference as if fully restated herein (hereinafter collectively also the "Prior Disclosures"). In exemplary embodiments, without limitation, each of the intravascular devices may comprise an expandable portion comprising a number of struts configured for selectively movement between a collapsed position and an expanded position. Such movement may be accomplished by way of an inner sleeve. The inner sleeve may be configured for sliding movement within a catheter tube which extends to a handle assembly, such as within a sheath. The inner sleeve may be connected to a distal end of the struts and/or a tip member at a distal end, and to a control element at the handle assembly at a proximal end. The inner sleeve may be configured to accommodate a guide wire.

The intravascular devices may comprise one or more fistula treatment elements. The fistula treatment elements may comprise one or more tissue modification elements. The tissue modification elements may be configured for scoring fibrotic tissue sometimes found in stenosed AV fistulas, such as by way of one or more longitudinally extending sharpened edges. In exemplary embodiments, without limitation, the tissue modification elements may comprise one or more features including a particular shape and/or size configured to efficiently score, incise, or otherwise modify such fibrotic tissue. For example, without limitation, the tissue modification elements may comprise an upper edge which is relatively further from an outer surface of an adjacent portion of an associated one of the struts at a first end thereof compared to a second end of the upper edge. In this manner, the tissue modification elements may define a tapered profile.

Alternatively, or additionally, the fistula treatment elements may comprise one or more irrigation and/or suction elements configured to remove and/or capture thrombi and/or particulate. In exemplary embodiments, without limitation, an irrigation and/or suction device may be provided at some or all of the struts of the expandable portion. For example, without limitation, the irrigation and/or suction device may comprise tubing or other fluid passageways which terminate at apertures at a portion of the inner sleeve extending within the expandable portion (e.g., between the struts) and/or at an opening between an outer surface of the inner sleeve and an inner surface of the catheter tube. Alternatively, or additionally, one or more hypotubes may be provided at some or all of the struts to provide such suction and/or irrigation. For example, without limitation, such hypotubes may be provided at interior surfaces of the struts. Alternatively, or additionally, one or more clips may be provided at, or adjacent to, one or more portions of the expandable portion and may be configured to receive tubing or other fluid passageways for such irrigation and/or suction devices.

Regardless, the irrigation and/or suction devices may be fluidly connected with, such as by way of the tubing or other fluid passageways, to one or more suction and/or irrigation equipment items. The equipment may include, but is not limited to, reservoirs, pumps, valves, adapters, filters, hoses, tubes, combinations hereof, or the like. Some or all of the equipment which may be located remote from the expandable portion, such as at a handle assembly and/or otherwise separate from the intervascular device but in fluid communication therewith, such as by way of one or more ports or other connection devices.

Various aspects of this invention will become apparent to those skilled in the art from the following detailed description of the preferred embodiments, when read in light of the accompanying drawings.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF THE PREFERRED EMBODIMENTS

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 1:
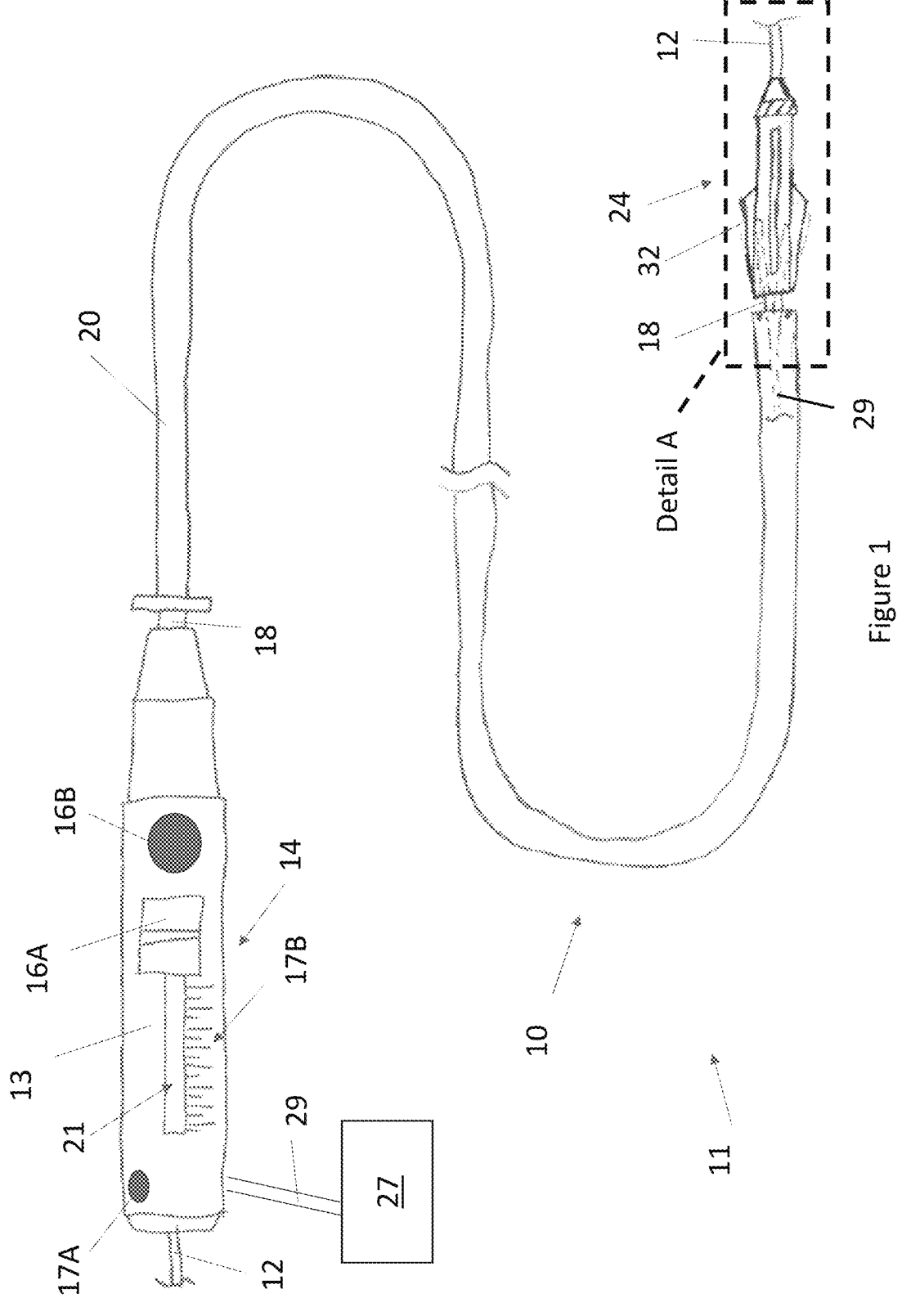
FIG. 1 is a plan view of an exemplary intravascular device for fistula treatment and related system, also illustrating detail A.

FIG. 1 illustrates a system 11 comprising an intravascular device 10 and related components for treating a fistula or surrounding area. The intravascular device 10 may comprise some or all of the components of the Prior Disclosures, the contents of which are hereby incorporated by reference as if fully restated herein.

The intravascular device 10 may comprise a handle subassembly 14. The handle subassembly 14 may comprise a housing 13. The handle subassembly 14 may be configured to accommodate a guide wire 12 passing through some or all of the handle subassembly 14.

The handle subassembly 14 may be configured to accommodate one or more tubes or other fluid passageways 29 (hereinafter also the "tubes") passing through some or all of the handle subassembly 14 or components thereof. The tube(s) 29 in exemplary embodiments may be fluidly connected to one or more irrigation and/or suction equipment items 27 (hereinafter also the "equipment"). Some or all of the equipment 27 may be located at the device 10, such as at or within the handle subassembly 14, or remote therefrom. The equipment 27 may comprise reservoirs, pumps, valves, adapters, filters, hoses, tubes, controllers, controls, gauges, displays, combinations thereof, or the like. The equipment 27 may comprise, or be configured to provide or hold, irrigation fluids such as water, saline, or the like (e.g., reservoirs, containers, pumps, pressurized tanks), and/or provide suction (e.g., pumps or vacuum generators) and/or store suctioned materials (e.g., reservoirs or containers). The equipment 27 may be part of the device 10, or may be separate therefrom and selectively connected thereto, such as by way of one or more ports, tubes, adapters, valves, combinations thereof, or the like.

The handle subassembly 14 may comprise one or more control elements 16. The control element(s) 16 in exemplary embodiments, without limitation, may comprise one or more levers, sliders, dials, knobs, buttons, motors, relays, touch pads, electronic controls, combinations thereof, or the like which are moveable or otherwise actuatable to operate an expandable portion 24 or other components of the device 10. At least some of the control element(s) 16A may be moveable or otherwise actuatable to operate some or all components of the expandable portion 24 in exemplary embodiments. Alternatively, or additionally, at least some of the control element(s) 16B may be moveable or otherwise actuatable to provide suction and/or irrigation at the fistula or surrounding area, such as by way of the equipment 27, the tubes 29, and/or other components of the device 10.

A catheter tube 18 may extend from the handle subassembly 14 to the expandable portion 24. The catheter tube 18 may be attached to, or extend within, the handle subassembly 14.

A sheath 20 may be provided, though such is not necessarily required. Some or all of the catheter tube 18 may extend through the sheath 20. The sheath 20 may be connected to the handle subassembly or be separate therefrom.

An inner sleeve 26 may extend within the catheter tube 18. The inner sleeve 26 may be configured for sliding movement within the catheter tube 18. The inner sleeve 26 may be connected to one or more of the control elements 16A, in exemplary embodiments without limitation, such that sliding or other actuation or movement of the control element(s) 16A is translated to corresponding movement of the inner sleeve 26. The inner sleeve 26 may be connected to, or form part of, some or all components of the expandable portion 24. The inner sleeve 26 may comprise a tube or other hollow member, though in other exemplary embodiments the inner sleeve 26 may comprise one or more solid members of any size or shape, such as but not limited to a wire, pushrod, linkage, combinations thereof, or the like.

The catheter tube 18, the inner sleeve 26, the sheath 20, and/or the guide wire 12 may comprise sufficiently flexible material to permit navigation of sinuous blood vessel within a patient's vascular system.

One or more indicators 17A may be provided, such as at the handle subassembly 14, the equipment 27, and/or a separate display or device, for indicating status of the equipment 27. The indicators 17A may be in wired or wireless connection with the equipment 27 and/or sensors within the device 10 for monitoring status of the irrigation and/or suction. For example, without limitation, pressure sensors may be provided within, or fluidly connected to, the tubes 29 to monitor operation of the suction and/or irrigation. The indicators 17A may comprise marking, electronic displays, gauges, lights, combinations thereof, or the like.

One or more indicators 17B may be provided, such as at the handle subassembly 14, for indicating status of the expandable portion 24. The indicators 17B may comprise marking on the housing 13 (e.g., for marking location of one or more of the control element(s) 16A relative to the housing), electronic displays, gauges, lights, combinations thereof, or the like.

The device 10 may be configured to automatically activate the irrigation and/or suction equipment 27, such as but not limited to, upon placement of the expandable portion 24 in the expanded position or retraction of the expandable portion 24, the sheath 20, combinations thereof, or the like. One or more sensors may be provided for detecting and/or reporting the same. For example, without limitation, levers, position sensors, switches, relays, combinations thereof, or the like may be provided for monitoring position of the control element(s) 16A and/or 16B, the sheath 20, accelerometers may be provided for detecting retraction, fluid sensors may be provided for detecting the presence of bodily fluids, strain gauges may be provided for detecting movement of the struts 30, pressure sensors may be provided at the struts 30 for detecting interaction with tissue, combinations thereof, or the like. Alternatively, or additionally, activation of the irrigation and/or suction equipment 27 may be made under manual control of a user, such as by way of one or more buttons, control interfaces, combinations thereof, or the like. The indicators 17A, 17B may be activated or deactivated to indicate status of the irrigation and/or suction equipment 27. One or more controllers may be provided at the device 10 and/or the equipment 27 for determining, operating, and/or reporting the same.

Referring additionally to FIG. 2 through FIG. 5, the expandable portion 24 may comprise one or more struts 30. In exemplary embodiments, the expandable portion 24 comprises three struts 30A, 30B, 30C. The struts 30A, 30B, 30C may be provided substantially equidistant about the inner sleeve 26. However, any number of struts 30 in any arrangement may be utilized. The struts 30, in exemplary embodiments, may each define a longitudinal axis that extends along a longitudinal axis of the expandable portion 24. The struts 30 may extend along a centerline of the guide wire 12, the inner sleeve 26, the catheter tube 18, and/or the sheath 20. The struts 30 in exemplary embodiments, without limitation, may comprise a relatively flattened outer surface. For example, without limitation, the struts may comprise an oval or rectangular shaped cross section, though any size, shape, or kind of struts 30 may be utilized. This may permit the outer surfaces of the struts to ride along tissue within the blood vessel and/or the blood vessel wall.

The expandable portion 24 may comprise a first common attachment component 28 and/or a second common attachment component 36. The struts 30 may be attached to the first common attachment component 28 at a first end thereof, and/or the second common attachment component 36 at a second end thereof. The inner sleeve 26 may be connected to the second common attachment component 36 in exemplary embodiments, without limitation. The first common attachment component 28 may be affixed to a distal end of the catheter tube 18 in exemplary embodiments. As the inner sleeve 26 may be configured for sliding movement while the catheter tube 18 remains fixed, the struts 30 may be configured to bow outwardly upon retraction of the inner sleeve 26 in exemplary embodiments, such as a result of compressive force(s) F1. In exemplary embodiments, without limitation, the control element(s) 16 may comprise a slider which is operable for sliding movement within a slot 21 on the handle subassembly 14 to cause sliding movement of the inner sleeve 26 within the catheter tube 18 to provide the compressive force(s) F1 and resulting movement of the struts 30 into an expanded position. In the expanded position (see e.g., FIGS. 2-5), a mid-portion of the struts 30 may bow outwardly away from the inner sleeve 26 such that the expandable portion 24 defines a maximum outer diameter, which is larger than a maximum outer diameter of the expandable portion 24 when in a collapsed position (see e.g., FIG. 1) where the struts 30 rest on, or extend along (such as but not limited to substantially parallel to) but are spaced apart from, the inner sleeve 26.

The first common attachment component 28, the second common attachment component 36, and/or the struts 30 may be integrally formed in exemplary embodiments. For example, without limitation, the first common attachment component 28, the second common attachment component 36, and/or the struts 30 may be formed in a sheet of material. Elongated slits 15 may be formed, such as by punching, cutting, combinations thereof, or the like, into the sheet of material to form the struts 30 and/or the first and/or second common attachment components 28, 36 and rolled. Multiple such slits 15A, 15B may be provided to form multiple struts 30A, 30B. Any number of slits 15 and accompanying struts 30 may be formed at any arrangement or spacing. In exemplary embodiments, the slits 15 are equidistantly spaced to form equal size struts 30.

The inner sleeve 26 may comprise components, such as but not limited to protrusions, configured to interact with components, such as but not limited to apertures 27, at the first common attachment component 28. Alternatively, or additionally, the catheter tube 18 may comprise components, such as but not limited to protrusions, configured to interact with components, such as but not limited to apertures 27, at the second common attachment component 36.

The first common attachment component 28, the second common attachment component 36, and/or the struts 30 may be integrally formed in exemplary embodiments. For example, without limitation, the first common attachment component 28, the second common attachment component 36, and/or the struts 30 may be form in a sheet of material, such as by punching, cutting, combinations thereof, or the like, and rolled. The inner sleeve 26 may comprise components, such as but not limited to protrusions, configured to interact with components, such as but not limited to apertures 19, at the first common attachment component 28. Alternatively, or additionally, the catheter tube 18 may comprise components, such as but not limited to protrusions, configured to interact with components, such as but not limited to apertures 19, at the second common attachment component 36.

In other exemplary embodiments, without limitation, the struts 30 may be joined to the first and/or second common attachment components 28, 36, such as by adhesive, welding, combinations thereof, or the like. The first and/or second common attachment components 28, 36 may be attached to the catheter tube 18 and the inner sleeve 26, respectively such as by protrusions on the catheter tube 18 and the inner sleeve 26 which frictionally engage with holes 19 in the first and/or second common attachment components 28, 36, respectively. Alternatively, or additionally, the first and/or second common attachment components 28, 36 may be attached to the catheter tube 18 and the inner sleeve 26 by adhesive, welding, combinations thereof, or the like.

The struts 30 may comprise one or more resiliently deformable materials such that the struts 30 are biased in the collapsed position, though such is not required. Alternatively, the struts 30 may be biased in the expanded position such that they are automatically expanded upon removal from the sheath 20. The struts 30 may comprise material which permits flexibility in bending to form an arch shape and bow outward. Alternatively, or additionally, the struts 30 may comprise one or more weakened regions, hinging areas, or the like which permit sections of the struts 30 to remain relatively non-deformed.

A tip member 40 may be provided. The tip member 40 may be connected to the second common connection component 36 and/or the inner sleeve 26. For example, the tip member 40 may be attached to the inner sleeve 26 at a position spaced apart from the second common connection component 36.

The device 10 may comprise one or more fistula treatment elements. For example, without limitation, one or more of the struts 30 may comprise, or have mounted thereto, one or more tissue modification element 32.

Some or all of the struts 30 may comprise one or more of the tissue modification elements 32. Each of the tissue modification elements 32 may comprise a protrusion, blade, sharpened edge, blunted edge, combination thereof, or the like which extends from an outer surface of a respective one of the struts 30. Each of the tissue modification element 32 may extend along a longitudinal axis of the respective one of the struts 30 to which it is attached or forms part of. Each of the tissue modification element 32 may extend along a longitudinal axis of the expandable portion 24. Each of the tissue modification elements 32 may extend along some, or all, of the respective one of the struts 30 to which it is provided on. In exemplary embodiments, without limitation, the tissue modification elements 32 may extend along a proximal portion of the struts 30, such as but not limited to along substantially half, or less than half, of the struts 30. Each of the tissue modification elements 32 may comprise an arcuate element, a blunted cuboid protrusion, a triangular prism, combinations thereof, or the like to name a few examples without limitation. Any size, shape, or type of the tissue modification elements 32 may be utilized to score, incise, cut, remove, or otherwise modify atherosclerotic material or other tissue or elements at a blood vessel or other treatment area. In exemplary embodiments, without limitation, the tissue modification elements 32 may be configured to create axially extending incisions in tissue located along an inner wall of the blood vessel when the expandable portion 24 is placed in the expanded position and retracted axially.

The tissue modification elements 32 may be coated with one or more medications, in exemplary embodiments, without limitation. In this manner, medication may be delivered at the time of incision.

The tissue modification elements 32 may be configured for scoring fibrotic tissue sometimes found in stenosed AV fistulas in exemplary embodiments, without limitation. For example, without limitation, the tissue modification elements 32 may comprise one or more features including a particular shape and/or size configured to efficiency score or otherwise incising such fibrotic tissue. Some or all of the tissue modification elements 32 may, in exemplary embodiments, without limitation, define a tapered profile. In exemplary embodiments, as particularly illustrated with regard to FIGS. 3A-3B, each of the fistula treatment elements 32 may comprise a lower portion 31 configured to reside within, or be attached to, a portion of the underlying one of the struts 30. Each of the fistula treatment elements 32 may comprise an upper portion 39 configured to physically interact with bodily tissue of a patient, such as but not necessarily limited to, stenosed tissue within a fistula, plaque within a blood vessel, combinations thereof, or the like.

Each of the fistula treatment elements 32 may comprise a leading edge 33, an upper edge 35, and/or a trailing edge 37. In exemplary embodiments, without limitation, each of the leading edge 33, the upper edge 35, and/or the trailing edge 37 may define straight, outer edges of the fistula treatment elements 32 which are interconnected to form a tapered profile. The tapered profile may be visible in a side view of the fistula treatment elements 32. For example, without limitation, the upper edge 35 may be lower at a first end thereof and higher at a second end thereof.

In exemplary embodiments, the leading edge 33 is a mid-level of length and a mid-level of steepness, as compared to the relatively long and less steep upper edge 35, and compared to the relatively short and steeper trailing edge 37.

The configuration of the fistula treatment elements 32 may be advantageous for cutting through the relatively fibrotic tissue sometimes found in AV fistulas. However, any size, shape, or type of the tissue modification elements 32 may be utilized to score, incise, cut, remove, or otherwise modify any type of kind of tissue or other material at a fistula or other treatment area.

In exemplary embodiments, without limitation, the leading edge 33 may extend between 30-55 degrees from an outer surface of the strut 30 to which it the tissue modification element 32 attached, the upper edge 35 may extend between 0-15 degrees relative to the outer surface of the strut 30 to which the tissue modification element 32 is attached, and/or the trailing edge 37 may extend between 30-90 degrees relative to the outer surface of the strut 30 to which the tissue modification element 32 is attached. The upper edge 35 may be between ¼ inch and 1 inch in length. The leading edge 33 may be between $\frac{1}{32}^{nd}$ inch and ¼ inch when measured along the respective strut 30 to which the tissue modification element 32 is attached. The trailing edge 37 may be between $\frac{1}{32}^{nd}$ inch and ¼ inch when measured along the respective strut 30 to which the tissue modification element 32 is attached. The leading edge 33 may extend from below or at the outer surface of the strut 30 to between 0.001" and ¼ inch in height in exemplary embodiments, without limitation. The upper edge 35 may have a height of between 0.002 inch and ¼ inch where it meets the leading edge 33 and between 0.002 inch and ½ inch where it meets the trailing edge 37. The trailing edge 37 may have a height of between 0.002 inch and ½ inch where it meets the upper edge 35 and extend to the outer surface of the strut 30, or below.

The tissue modification element 32 may have an overall length of between ¼ inch and ¾ inch, in exemplary embodiments, without limitation. The tissue modification element 32 may be recessed between 0.0005 and 0.01 inches below an outer surface of a respective one of the struts 30. The tissue modification element 32 may have an overall thickness of between 0.0005 and 0.01 inches in exemplary embodiments, without limitation. The expandable portion 24 may have an outer diameter of between 0.005 and 0.1 inches in exemplary embodiments, without limitation when formed. The struts 30 may have a thickness of between 0.005 and 0.1 inches in exemplary embodiments, without limitation. The slits 15 may be between 1.5 and 0.5 inches in exemplary embodiments, without limitation. The slits 15 may have a thickness of between 0.0005 and 0.01 inches in exemplary embodiments, without limitation.

The lower portion 31 may be smaller than the upper portion 39 in length, though such is not required. The lower portion 31 may be recessed within the strut 30, though such is not required. The strut 30, for example without limitation, may comprise a recess or aperture for accommodating the lower portion 31. Adhesive, welding, or the like may be used to secure the tissue modification element 32 to the strut 30.

Exemplary dimension drawings illustrating exemplary embodiments of the expandable portion 24 and specifically the tissue modification elements 32 is provided at FIGS. 4B-4F, without limitation. The angles, sizes, shapes, and dimensions shown and/or described herein are merely exemplary and are not intended to be limiting. Any size, shape or configuration of the tissue modification element 32 may be utilized.

Figure 2:
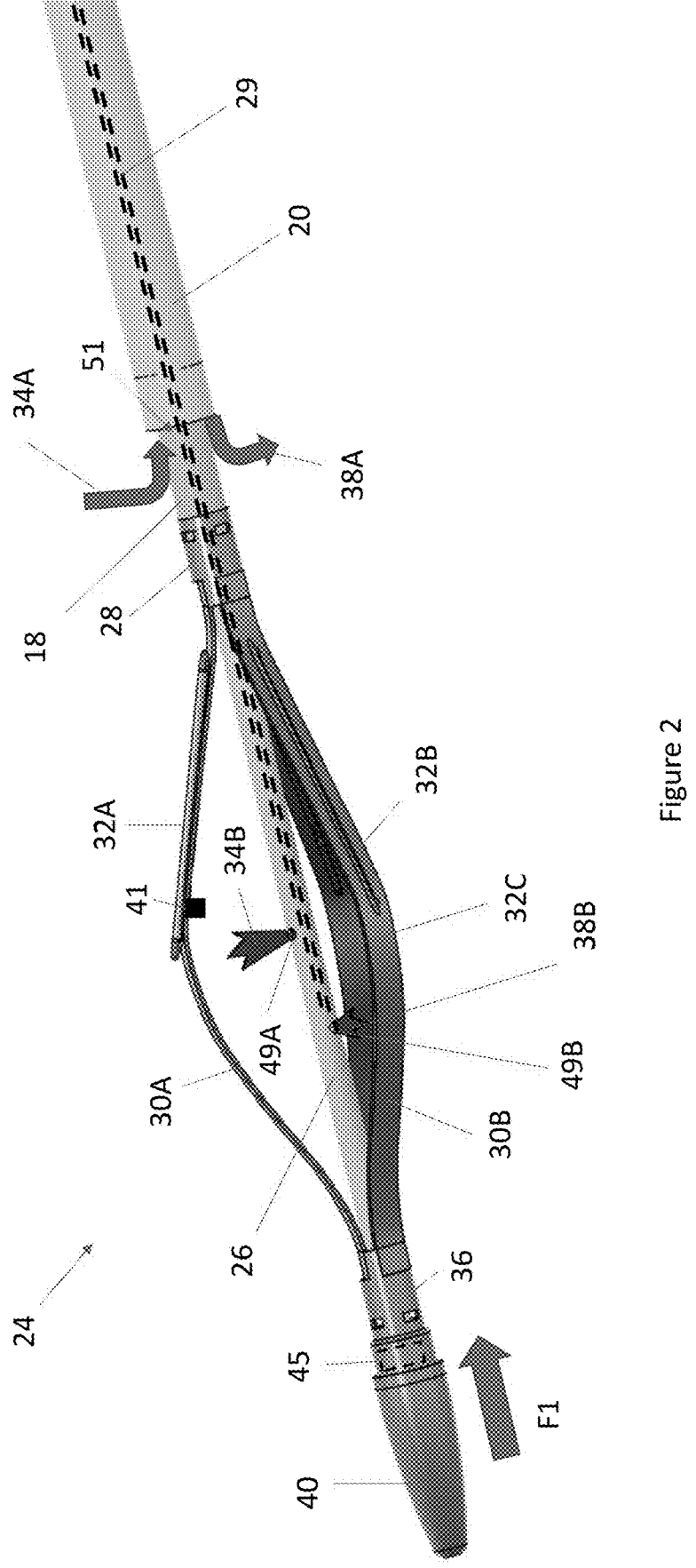
FIG. 2 is a detailed perspective view of an exemplary expandable portion of detail A of FIG. 1.

As shown with particular regard to FIG. 2, the fistula treatment elements may, alternatively or additionally, comprise one or more tubes 29 and related equipment 37, such as for providing irrigation 34 and/or suction 38. The irrigation 34 and/or suction 38 may be configured to release and/or capture thrombi and/or particulate. In exemplary embodiments, one or more ports 49 may be provided for the introduction of irrigation fluid 34 and/or suction of materials 38. One or more ports 49 may, in exemplary embodiments without limitation, be provided at a portion of the inner sleeve 26 extending within the expandable portion 24, such as but not limited to, between the struts 30. The ports 49 may be fluidly connected to the equipment 37 by way of the tube(s) 29, which may extend through the inner sleeve 26, the catheter tube 18, the sheath 18, and/or the handle subassembly 14. In exemplary embodiments, without limitation, a first port 49A may be provided at the inner sleeve 26 for releasing irrigation fluid 34B. A second port 49B may be provided at the inner sleeve 26 for capturing suctioned materials 38B.

Alternatively, or additionally, one or more gaps 51 may be provided between an outer surface of the catheter tube 18 and an inner surface of the sheath 20. These gap(s) 51 may be configured to permit the introduction of irrigation fluid 38A and/or suction of materials 34A in exemplary embodiments. Separate ports 49 for the introduction of irrigation fluid 38A and/or suction of materials 34A may alternatively, or additionally, be provided.

Multiple tubes 29 may be provided which connect with one another to form one or more larger tubes 29, though such is not required. Some or all of the ports 49 or gaps 51, tubes 29, and/or equipment 27 may be used for both irrigation fluid and suction or materials, such as but not limited to on an alternating basis, though such is not required. In other exemplary embodiments, certain of the ports 49 or gaps 51, tubes 29, and/or equipment 27 may be dedicated for irrigation while other of the ports 49 or gaps 51, tubes 29, and/or equipment 27 may be dedicated for suction.

In yet other exemplary embodiments, without limitation, one or more clips 41 may be provided at or adjacent to one or more portions of the expandable portion 24 and may be configured to receive tubing 29 or other fluid passageways for such irrigation and/or suction devices. Combinations of such features the same may be utilized.

Figure 2B:
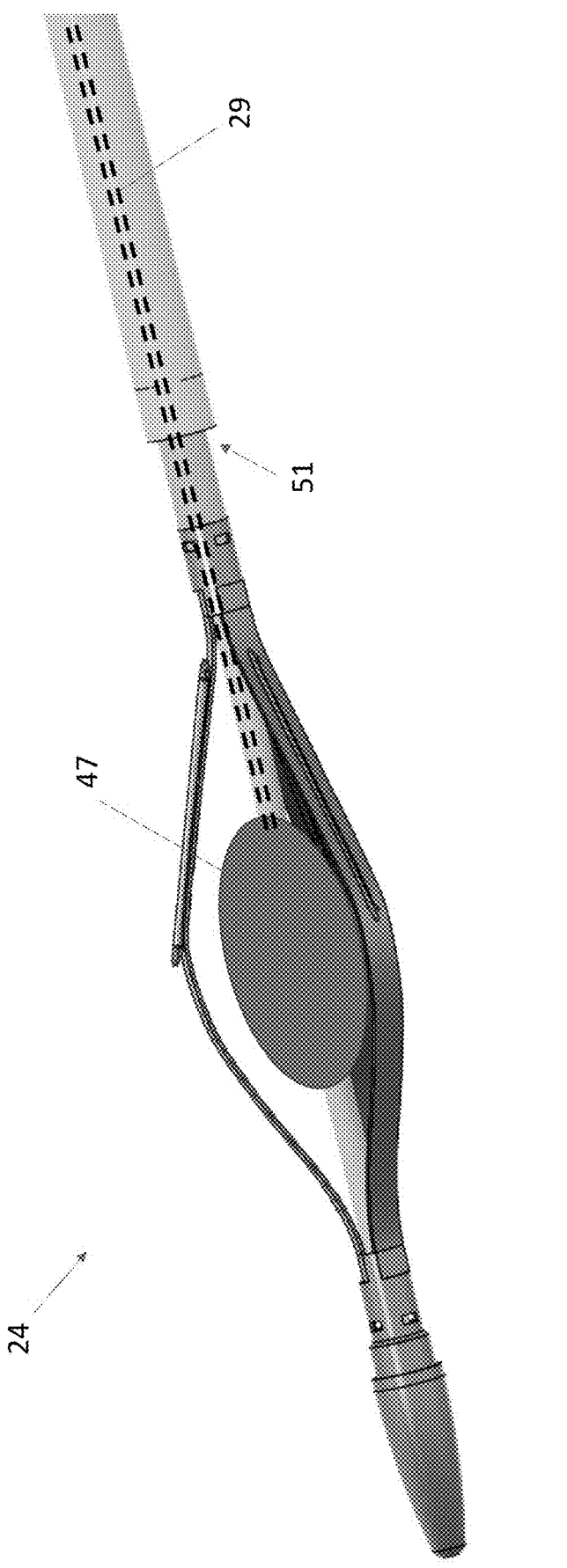
FIG. 2B is a detailed perspective view of another exemplary embodiment of the expandable portion of detail A of FIG. 1.
Figures 3A, 3B:
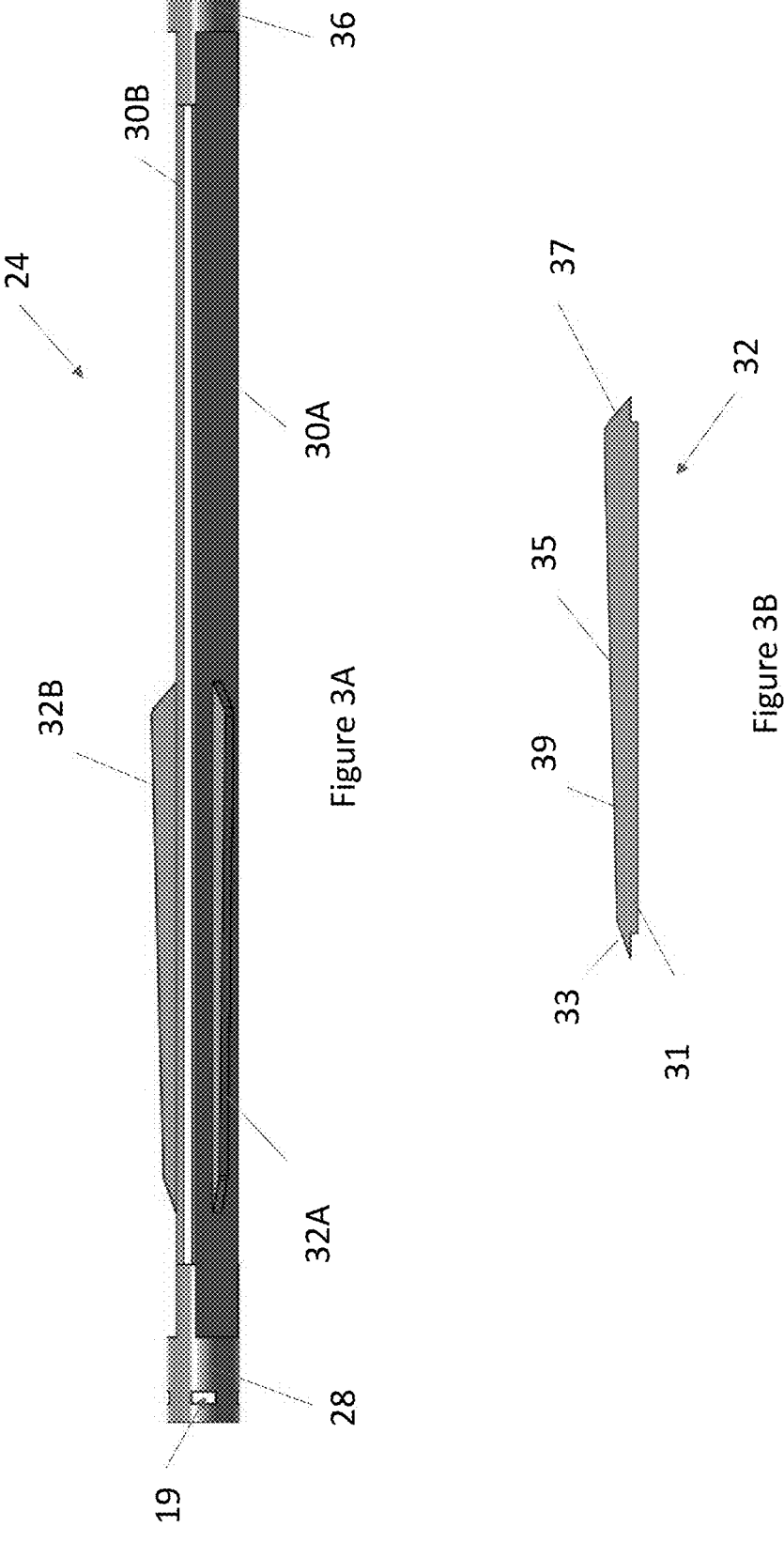
FIG. 3A is a side view of an exemplary embodiment of the expandable portion FIG. 2 with certain components of the device and system omitted.
FIG. 3B is a side view of the exemplary tissue modification element of FIG. 3A illustrated in isolation.
Figures 4A, 4B, 4C:
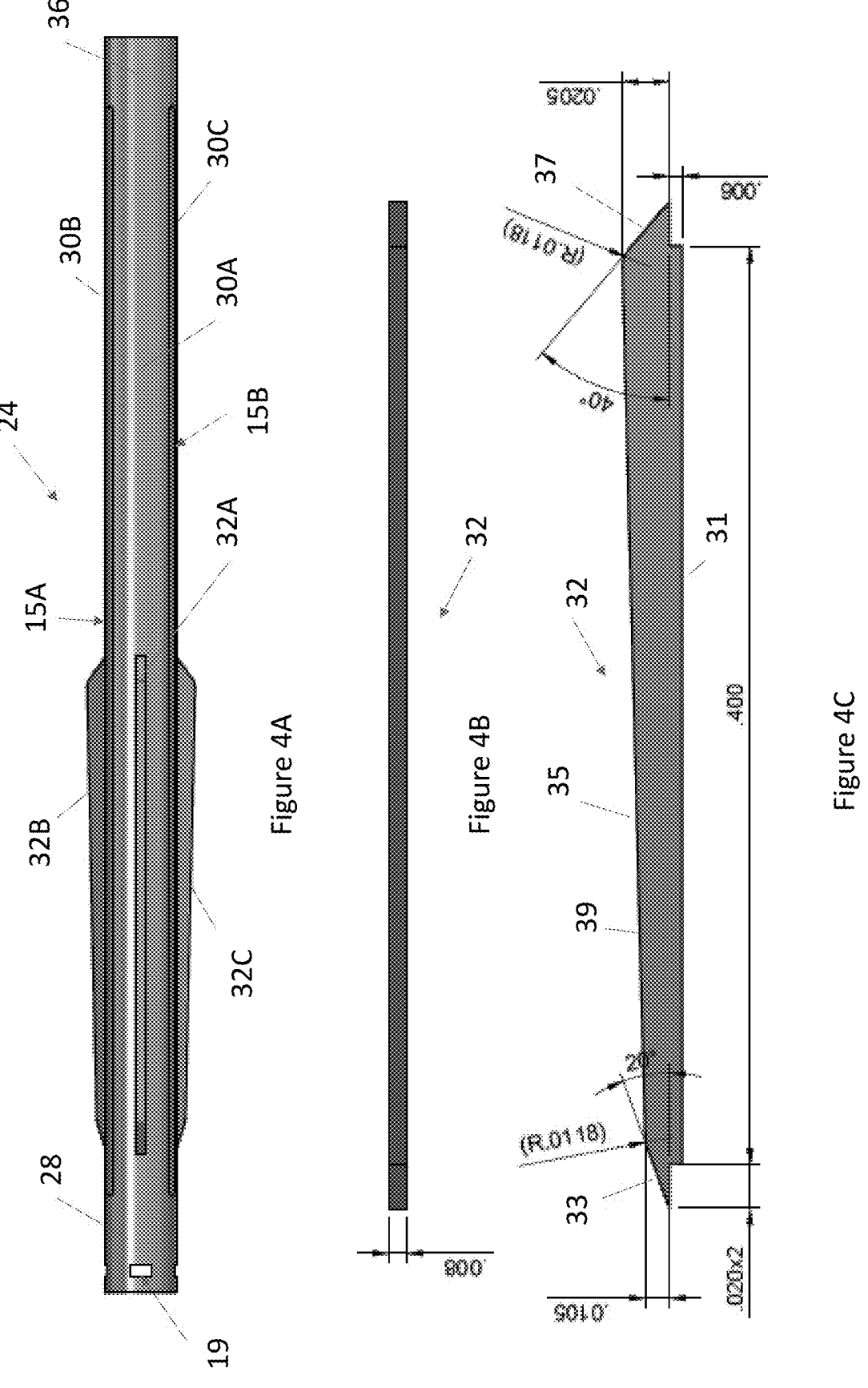
FIG. 4A is a side view of another exemplary embodiment of the expandable portion FIG. 2 with certain components of the device and system omitted.
FIG. 4B is a bottom view of the exemplary tissue modification element of FIG. 4A illustrated in isolation.
FIG. 4C is a side view of the exemplary tissue modification element of FIG. 4A illustrated in isolation.
Figures 4D, 4E, 4F:
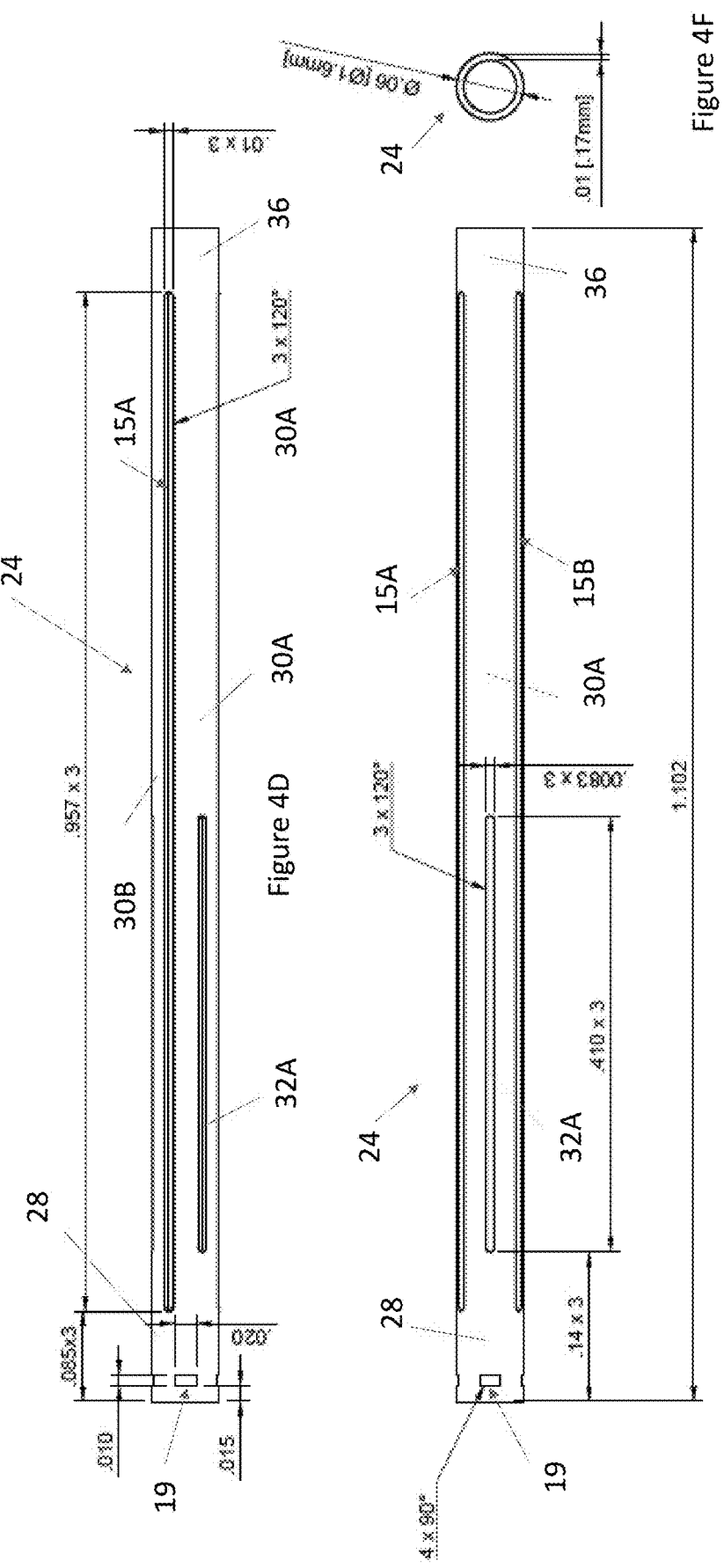
FIG. 4D is a line drawing of the expandable portion of FIG. 4A providing certain dimensions and measurement.
FIG. 4E is another dimensioned line drawing of the expandable portion of FIG. 4A illustrating other dimensions and measurements.
FIG. 4F is a front view of the line drawing of FIG. 4D illustrating other dimensions and measurements.
Figure 5:
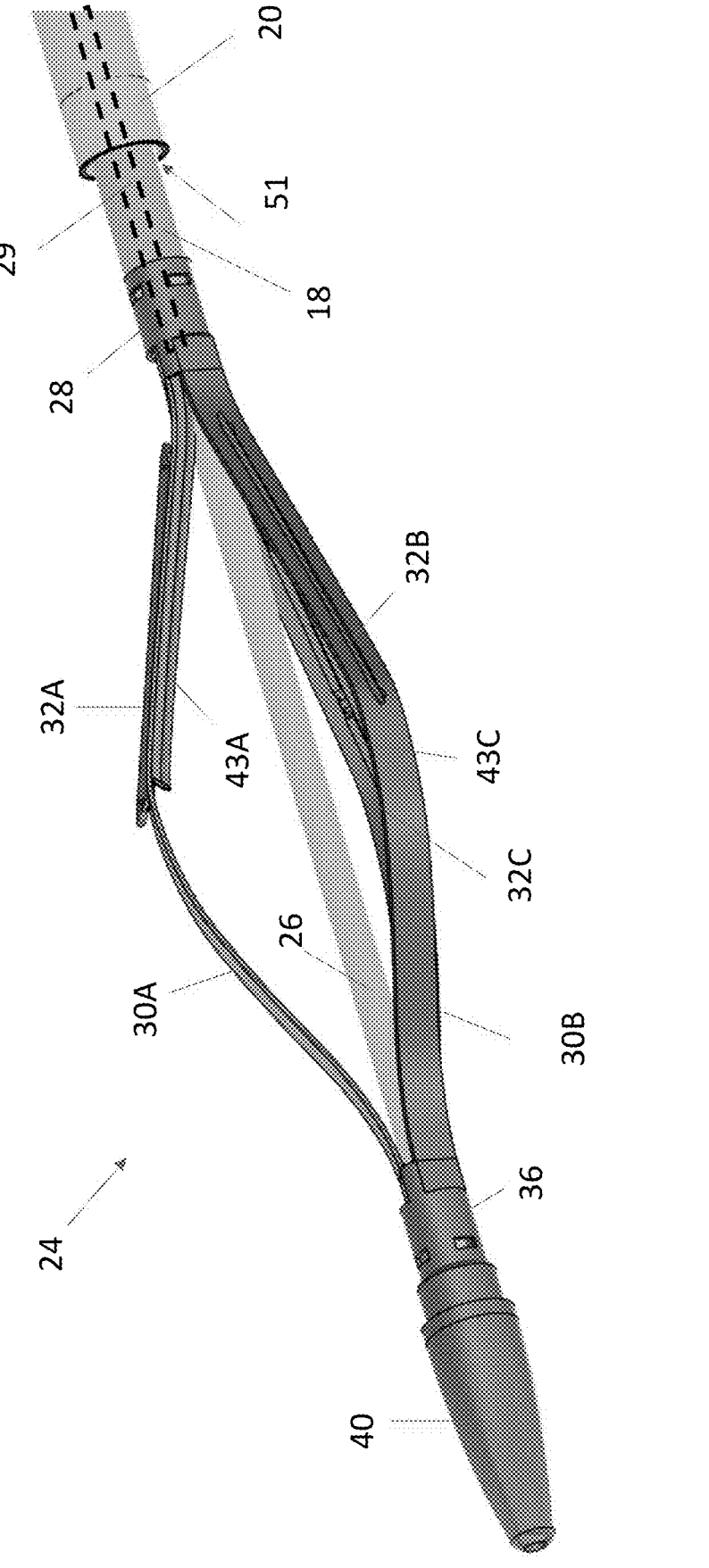
FIG. 5 is a detailed perspective view of another exemplary embodiment of the expandable portion of detail A of FIG. 1.

As illustrated with particular regard to FIG. 2B, Alternatively, or additionally, a balloon 47 may be provided within struts 30 configured for selective inflation and deflation to cause movement of said expandable portion 24 between the expanded and collapsed positions. The tubes 29 may be configured to provide fluid communication between the balloon 47 the equipment 27 to provide or remove inflation fluids from the balloon 47. The ports 49 may facilitate the introduction or removal of such inflation fluids from the balloon 47. The gap(s) 51 may be provided for the introduction of irrigation fluids and/or suction forces and removal of material, though such is not required. The irrigation fluids and/or suction forces may comprise the same or different fluids and be operated by the same or different equipment 27 and/or connected to the same or different tube(s) 29.

As illustrated with particular regard to FIG. 4, alternatively, or additionally, one or more hypotubes 43 may be provided at some or all of the struts 30 to provide such suction and/or irrigation. The hypotubes 43 may be connected to the struts 30 by way of the clips 41, may be integrally formed therewith, permanently affixed thereto, combinations thereof, or the like. In exemplary embodiments, without limitation, such hypotubes 43 may be provided at interior surfaces of the struts 30. For example, without limitation, a hypotube 43A, 43B, 43C may be provided at an interior side of each of the struts 30A, 30B, 30C, though any number of hypotubes 43 or some or all of any number of struts 30 may be utilized. The hypotubes 43 may be connected to one or more of the tubes 29 to provide the suction and/or irrigation.

Notably, the device 10 may be utilized without the irrigation/suction elements, which are optional. For example, without limitation, the device 10 may be used without one or more of the hypotubes 43, the clips 41 ports 49 or gaps 51, tubes 29, and/or equipment 27. In this manner, the device 10 may utilize the tissue modification elements 32 to perform treatment. For example, without limitation, the device 10 may be used to modify tissue, such as but not limited to, scoring tissue built up in fistulas, such as in preparation for subsequent angioplasty and/or stenting. Alternatively, or additionally, the device 10 may be utilized without the tissue modification elements 32, which are optional, and/or the expandable portion 24 may be placed in a collapsed position so that the tissue modification elements 32 are not contacting and modifying tissue. In this manner, the irrigation/suction may be utilized to perform treatment. In exemplary embodiments, without limitation, both the tissue modification elements 32 and the irrigation/suction elements are provided and/or the expandable portion 24 is placed in the expanded position so that tissue modification and irrigation and/or suction may be provided as part of the treatment.

A limiter 45 may be provide between the second common connection component 36 and the tip member 40. Alternatively, the limiter 45 may be provide between the struts 30 and the tip member 40. The limiter 45 may be configured to cause the struts 30 to expand only to a predetermined size when placed in the expanded position. The limiter 45 may comprise one or more springs configured to provide sufficient forces (e.g., F1) axially along said inner sleeve 26 and/or catheter tube 18 towards said handle assembly 14 to force said struts 30 to bow outwardly when said struts 30 are exposed form the sheath 20 for expansion into the expanded position. In this way, the limiter 45 may act to bias the expandable portion 24 in the expanded position. Because the amount of force applied by the limiter 45 may be predetermined and/or limited, this may prevent the struts 30, and attached tissue modification elements 32, from expanding beyond a desired diameter and/or providing more forces or pressure than desired. This arrangement may permit retraction of the sheath 20 beyond the expandable portion 24 without necessarily changing the size of the expandable portion 24 and/or the forces exerted by the tissue modification elements 32. This may be particularly advantageous where the otherwise tortuous nature of the vascular system and/or other characteristics of the access site may make precise control of the size of the expandable portion 24, such as by movement of the control element(s) 16 difficult. This may also prevent over expansion of the expandable portion 24 and/or over exertion of forces at the tissue modification elements 32. The limiter 45 is not required. The tip member 40 may be configured to accommodate the guide wire 12.

In other exemplary embodiments, without limitation, a second end of the struts 30 may be free, such that the second common connection component 36 is not required. The struts 30 in such embodiments may be configured for cantilevered operation such as provided in the Prior Disclosures. Some or all of the expandable portion 24 may be formed and/or assembled as provided in the Prior Disclosures.

The sheath 20, in exemplary embodiments without limitation, may be configured for sliding movement so as to selectively expose, or cover, the expandable portion 24. One or more control element(s) 16 may be provided on the handle subassembly 14 for moving the sheath 20, though such is not required. For example, without limitation, the sheath 20 may be manually slidable. In other exemplary embodiments, without limitation, the sheath 20 may be fixed, and the expandable portion 24 may be moveable relative to the sheath 20.

Figure 6:
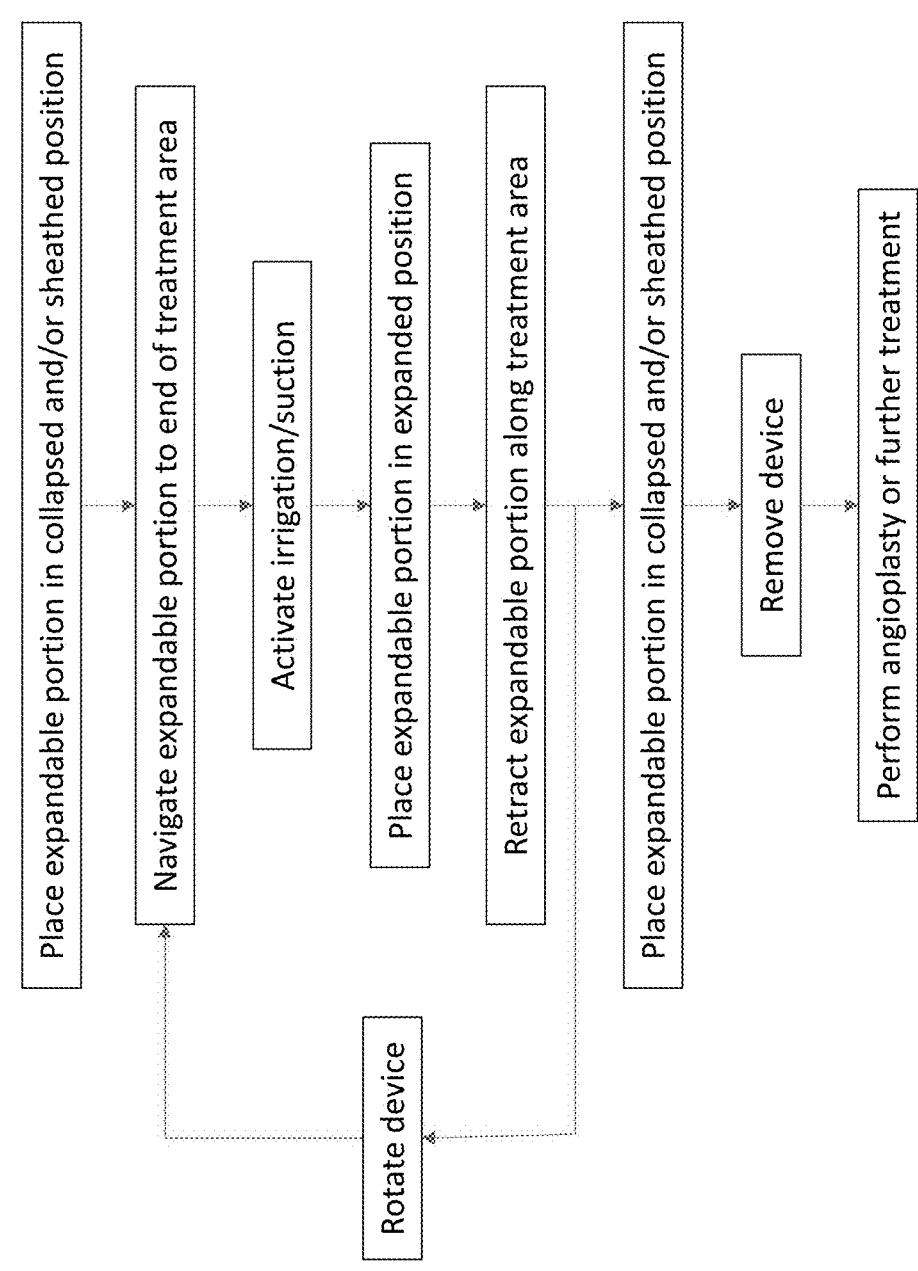
FIG. 6 is a flow chart for an exemplary method of utilizing the devices and systems of FIGS. 1-5.

Referring additionally to FIG. 6, in exemplary embodiments, without limitation, the guide wire 12 may be introduced to the patient's vascular system and advanced to a treatment area. The guide wire 12 may be advanced to a distal end of the treatment area, or beyond, to give room for maneuvering. Part of the device 10, such as the expandable portion 24, may be introduced to the patient's vascular system in the collapsed and/or sheathed state and advanced in the collapsed and/or sheathed state to a treatment area, such as a fistula or area of stenosis (e.g., plaque or other tissue accumulation) within a blood vessel. The treatment area may be a peripheral artery or fistula, for example without limitation-any location, or multiple locations, within the patient's vascular system may be treated.

The device 10 may be advanced along the guide wire 12 to the treatment area. For example, without limitation, the expandable portion 24 may be manually fed over the guide wire 12 which may extend through the inner sleeve 26 and out the handle subassembly 14. Alternatively, or additionally, a distal portion of the inner sleeve 26 may comprise one or more holes, slits, or the like for allowing the guide wire 12 to enter and exit a portion of the expandable portion 24 without necessarily extending through all of the inner sleeve 26 and/or the handle subassembly 14.

The expandable portion 24 may be unsheathed and/or placed in the expanded position at an end of the treatment area and moved along the treatment area. The expandable portion 24 may be moved along the guide wire 12 extending therethrough. The expandable portion 24, and particularly the tissue modification elements 32, may modify the tissue located along interior walls of the blood vessel, such as by scoring as the expandable portion 24 is retracted. The expandable portion 24 may be initially positioned at a distal end of the treatment area and retracted therethrough, such as along the guide wire 12, while in the expanded position to score tissue located therein. This may permit movement of the expandable portion 24 counter to blood flow, though such is not required. Scoring may include creation of longitudinally extending slits in the tissue. Doing so may break surface tension in the tissue, resulting in luminal gain by itself and/or in combination with subsequent angioplasty, such as performed by a separate device at the treatment area once the expandable portion 24 is removed. Subsequent angioplasty is not necessarily required. Other treatments may also be simultaneously or subsequently performed, including but not limited to, imaging, stenting, medication delivery, combinations thereof, or the like. In exemplary embodiments, without limitation, the outer surface of the struts 30 may ride along the tissue, such as while the expandable portion 24 is retracted. This may limit a penetrative depth of the tissue modification elements 32 into the tissue.

At any time, but particularly some or all of a time the expandable portion 24 is at or retracted through the treatment area, some or all of the equipment 27 may be activated to provide irrigation and/or suction at the expandable portion 24. In this fashion, thrombi and/or particulate may be released and/or captured. This may provide for some level of tissue removal (e.g., atherectomy) at the treatment area. The irrigation and/or suction may be periodically or selectively deactivated, though such is not required and the irrigation and/or suction may be left on continuously for some or all of a treatment procedure. One or both of irrigation and/or suction may be provided some or all of the time. For example, without limitation, just one of irrigation and suction may be provided, both may be provided on an alternating basis, and/or both may be provided simultaneously. The device 10 may be configured to automatically activate the irrigation and/or suction equipment 27, such as but not limited to, upon placement of the expandable portion 24 in the expanded position or retraction of the expandable portion 24, the sheath 20, combinations thereof, or the like. Alternatively, or additionally, activation of the irrigation and/or suction equipment 27 may be made under manual control of a user.

Multiple passes of the expandable portion 24 may be made, though a single pass may be utilized. The expandable portion 24 may be rotated between such passes to create additional slits within the plaque or other tissue. Such rotation may be performed at various times, including before repositioning the expandable portion 24 at the distal end of the treatment area, after repositioning the expandable portion 24 at the distal end of the treatment area, while repositioning the expandable portion 24 at the distal end of the treatment area, while retracting the expandable portion 24, combinations thereof, or the like. The expandable portion 24 need not be repositioned at the same start or end point for each retraction pass. Multiple passes may be made without rotation, such as to create deeper slits, wider slits, additional slits in close proximity, break through harder tissue, with different pressures or forces applied, different levels of expansion provided at the expandable portion 24, combinations thereof, or the like. Irrigation and/or suction may be provided during some, all, or none of such passes.

After completing treatment, the expandable portion 24 may be removed from the treatment area and/or from the patient. Angioplasty may subsequently be performed, such as by way of one or more separate devices, though such is not required. Alternatively, or additionally, stents or other devices may be placed to help maintain the achieved luminal gains or other medical results. Such stents or other devices may be placed by the device 10, angioplasty device, or other device.

The struts 30, the tissue modification elements 32, and/or hypotubes 43 may be coated with one or more materials, though such is not required. Such materials may comprise lubricious and/or medicated coatings in exemplary embodiments, without limitation.

Components of the device 10 may comprise one or more materials such as, but not limited to, one or more metals (e.g., nickel titanium alloy), polymers, combinations thereof, or the like. Materials utilized may be biocompatible, sterilizable, combinations thereof, or the like. Components of the device 10 may be integrally formed or joined, such as by welding, brazing, adhesion, mechanical fasteners, combinations thereof or the like.

While sometimes described as being used for treating fibrotic stenosis in fistulas, the system 11 and/or device 10 may be used to treat any type of kind of tissue in any location, such as but not limited to other bodily tissue within a patient's vascular system. For example, without limitation, the system 11 and/or device 10 may be used to treat plaque in blood vessels, such as sometimes results from peripheral artery disease.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention.

Certain operations described herein may be performed by one or more electronic devices. Each electronic device may comprise one or more processors, electronic storage devices, executable software instructions, combinations thereof, and the like configured to perform the operations described herein. The electronic devices may be general purpose computers or specialized computing devices. The electronic devices may comprise personal computers, smartphone, tablets, databases, servers, or the like. The electronic connections and transmissions described herein may be accomplished by wired or wireless means. The computerized hardware, software, components, systems, steps, methods, and/or processes described herein may serve to improve the speed of the computerized hardware, software, systems, steps, methods, and/or processes described herein.

What is claimed is:

1. An intravascular device for treating a fistula, said intravascular device comprising:
   a handle assembly;
   a catheter tube extending from said handle assembly;
   an expandable portion connected to said catheter tube and selectively movable between a first position and an expanded position; and
   one or more incising elements for creating axially extending incisions in material accumulated at the fistula upon axial retraction of the expandable portion while in the expanded position through at least some of the fistula, wherein said one or more incising elements are located at said expandable portion and extend along a longitudinal axis of said expandable portion, each of said one or more incising elements comprising a leading edge, an upper edge, and a trailing edge, where said leading edge, said upper edge, and said trailing edge are interconnected straight edges forming a tapered profile from a side view thereof such that a first end of the upper edge adjoining the leading edge is relatively further from an adjacent portion of an outer surface of said expandable portion compared to a second end of the upper edge adjoining the trailing edge;
   wherein said leading edge of each of said one or more incising elements extends at an angle between 10 and 30 degrees from the adjacent portion of the outer surface of the expandable portion, said trailing edge of each of said one or more incising elements extends at a 30-50 degree angle from the outer surface of the adjacent portion of the expandable portion, and said upper edge extends at a non-zero angle relative to the outer surface of the adjacent portion of the expandable portion.

2. The intravascular device of claim 1 wherein:
said expandable portion comprises a plurality of struts;
each of said struts extend along the longitudinal axis of the expandable portion;
each of the struts comprises one of the incising elements; and
each of said incising elements extend along an outer surface of an associated one of the struts.

3. The intravascular device of claim 2 wherein:
each of said incising elements extend along a proximal half of the associated one of the struts.

4. The intravascular device of claim 2 further comprising:
a control element located at said handle assembly; and
an inner sleeve attached to said control element at a first end and a distal end of said struts at a second end such that actuation of said control element causes sliding movement of said inner sleeve, which causes movement of said struts between said first position, where said struts extend along an outer surface of said inner sleeve, and said expanded position, where said struts bow outwardly away from said inner sleeve.

5. The intravascular device of claim 1 wherein:
said leading edge of each of said one or more incising elements has a maximum height of between 0.005 and 0.02 inches; and
said trailing edge of each of said one or more incising elements has a maximum height of between 0.01 and 0.03 inches.

6. The intravascular device of claim 1 wherein:
each of said one or more incising elements has an overall length of between 0.2 and 0.6 inches.

7. The intravascular device of claim 1 further comprising:
one or more hypotubes provided at said expandable portion for providing irrigation or suction.

8. The intravascular device of claim 7 wherein:
said expandable portion comprises a plurality of struts; and
one of said hypotubes is provided at an interior surface of one of said struts.

9. The intravascular device of claim 4 further comprising:
one or more items of equipment configured to provide at least one of irrigation fluid and suction force when activated;
one or more ports provided at a portion of said inner sleeve residing within said expandable portion; and
one or more tubes extending from said equipment to each of said one or more ports to provide fluid communication with said one or more items of equipment to provide the at least one of irrigation fluid and suction force at said one or more ports when said one or more items of equipment are activated.

10. The intravascular device of claim 4 further comprising:
one or more items of equipment configured to provide at least one of irrigation fluid and suction force when activated;
a gap provided between an outer surface of said inner sleeve and an inner surface of said catheter tube; and
one or more tubes extending from said one or more items of equipment to said gap to provide the at least one of the irrigation fluid and suction force at said gap when said one or more items of equipment is activated.

11. The intravascular device of claim 1 further comprising:

one or more items of equipment configured to provide at least one of irrigation fluid and suction force when activated;

one or more tubes extending from said equipment to said expandable portion; and one or more clips provided at said expandable portion and configured to secure a distal end of said tubes to provide the at least one of irrigation fluid and suction force at said expandable portion when said one or more items of equipment are activated.

12. A method for treating a fistula using the intravascular device of claim 1, said method comprising the steps of:

placing the expandable portion of the intravascular device in the first position;

navigating the expandable portion to a distal portion of the fistula;

placing the expandable portion in the expanded position such that the incising element having the tapered profile contacts tissue located along a wall of the fistula;

retracting the expandable portion along the fistula to create axially extending incisions in said tissue.

13. The method of claim 12 further comprising the steps of:

providing irrigation at the fistula by activating equipment fluidly connected to apertures at said expandable portion; or providing suction of the tissue and other material at the fistula by activating equipment fluidly connected to apertures at said expandable portion.

14. The method of claim 12 further comprising the steps of:

removing said expandable portion from said fistula;

introducing a balloon in a deflated state to said fistula; and inflating said balloon at said fistula to compress said incised tissue.

15. An intravascular device comprising:

a handle assembly comprising a control element;

a catheter tube extending from said handle assembly;

an inner sleeve located within the catheter tube and having a first end attached to said control element;

an expandable portion connected to said catheter tube, said expandable portion comprising a plurality of struts, each extending along the longitudinal axis of the expandable portion and selectively moveable between a first position where said struts extend longitudinally along the inner sleeve, and an expanded position where a mid-portion of each of said struts is moved away from the inner sleeve, wherein a second end of the inner sleeve is attached to a distal end of said expandable portion such that actuation of said control element causes sliding movement of said inner sleeve, which causes movement of said struts between said first position and said expanded position;

incising elements for creating axially extending incisions in tissue upon axial retraction of the expandable portion while in the expanded position through at least some of an intravascular passageway, each located at one of said struts and extending longitudinally along an outer surface of, and a longitudinal axis of, an associated one of said struts, wherein each of said incising elements comprises a tapered profile;

at least one of: one or more hypotubes provided at said expandable portion, and one or more ports provided at a portion of said inner sleeve located within said expandable portion; and one or more fluid passageways extending from the at least one of the one or more hypotubes and the one or more ports to provide fluid communication with one or more items of equipment configured to provide at least one of irrigation fluid and suction force at the at least one of the one or more hypotubes and the one or more ports when connected and activated.

16. The intravascular device of claim 15 wherein:

said one or more fluid passageways comprising one or more tubes extending from:

the at least one of the one or more hypotubes and the one or more ports to the one or more items of equipment; or said one or more items of equipment to a gap provided between an outer surface of said inner sleeve and an inner surface of said catheter tube.

17. An intravascular device for treating a fistula, said intravascular device comprising:

a handle assembly;

a catheter tube extending from said handle assembly;

an expandable portion connected to said catheter tube and selectively movable between a first position and an expanded position;

one or more incising elements for creating axially extending incisions in material accumulated at the fistula upon axial retraction of the expandable portion while in the expanded position through at least some of the fistula, said one or more incising elements located at said expandable portion and extending along a longitudinal axis of said expandable portion, each of said one or more incising elements comprising a tapered profile from a side view thereof where a first end of an upper edge is relatively further from an adjacent portion of an outer surface of said expandable portion at a first end of the upper edge compared to a second end of the upper edge;

one or more items of equipment configured to provide at least one of irrigation fluid and suction force when activated;

one or more tubes extending from said equipment to said expandable portion; and one or more clips provided at said expandable portion and configured to secure a distal end of said tubes to provide the at least one of irrigation fluid and suction force at said expandable portion when said one or more items of equipment are activated.

18. An intravascular device for treating a fistula, said intravascular device comprising:

a handle assembly;

a catheter tube extending from said handle assembly;

an expandable portion connected to said catheter tube and selectively movable between a first position and an expanded position; and one or more incising elements for creating axially extending incisions in material accumulated at the fistula upon axial retraction of the expandable portion while in the expanded position through at least some of the fistula, said one or more incising elements located at said expandable portion and extending along a longitudinal axis of said expandable portion, each of said one or more incising elements comprising a leading edge, an upper edge, and a trailing edge, where said leading edge, said upper edge, and said trailing edge are interconnected straight edges forming a tapered profile from a side view thereof where a first end of the upper edge adjoining the leading edge is relatively further from an adjacent portion of an outer surface of said expandable portion compared to a second end of the upper edge adjoining the trailing edge;

wherein said leading edge of each of said one or more incising elements has a maximum height of between 0.005 and 0.02 inches, and said trailing edge of each of said one or more incising elements has a maximum height of between 0.01 and 0.03 inches.

19. The intravascular device of claim 18 wherein:

said leading edge of each of said one or more incising elements extends at an angle between 10 and 30 degrees from an adjacent portion of the outer surface of the adjacent portion of the expandable portion;

said trailing edge of each of said one or more incising elements extends at a 30-50 degree angle from the outer surface of the adjacent portion of the expandable portion; and said upper edge extends at a non-zero angle relative to the outer surface of the adjacent portion of the expandable portion.

20. An intravascular device for treating a fistula, said intravascular device comprising:

a handle assembly;

a catheter tube extending from said handle assembly;

an expandable portion connected to said catheter tube and selectively movable between a first position and an expanded position;

one or more hypotubes provided at said expandable portion for providing irrigation or suction; and one or more incising elements for creating axially extending incisions in material accumulated at the fistula upon axial retraction of the expandable portion while in the expanded position through at least some of the fistula, said one or more incising elements located at said expandable portion and extending along a longitudinal axis of said expandable portion, each of said one or more incising elements comprising a tapered profile from a side view thereof where a first end of an upper edge is relatively further from an adjacent portion of an outer surface of said expandable portion compared to a second end of the upper edge.

21. The intravascular device of claim 20 wherein:

said expandable portion comprises a plurality of struts; and one of said hypotubes is provided at an interior surface of one of said struts.

* * * * *